(12) United States Patent
Iwata

(10) Patent No.: US 8,664,626 B2
(45) Date of Patent: Mar. 4, 2014

(54) PARTICLE BEAM THERAPY SYSTEMS AND THE METHODS FOR TIME-SHARING IRRADIATION

(71) Applicant: Mitsubishi Electric Corporation, Chiyoda-ku (JP)

(72) Inventor: Takaaki Iwata, Tokyo (JP)

(73) Assignee: Mitsubishi Electric Corporation, Chiyoda-Ku, Tokyo (JP)

(*) Notice: Subject to any disclaimer, the term of this patent is extended or adjusted under 35 U.S.C. 154(b) by 0 days.

(21) Appl. No.: 13/897,930

(22) Filed: May 20, 2013

(65) Prior Publication Data

US 2013/0253253 A1 Sep. 26, 2013

Related U.S. Application Data

(62) Division of application No. 13/119,594, filed as application No. PCT/JP2010/065515 on Sep. 9, 2010, now Pat. No. 8,481,979.

(51) Int. Cl.
*A61N 5/00* (2006.01)

(52) U.S. Cl.
USPC ...................................... 250/492.1

(58) Field of Classification Search
USPC ............... 250/492.1, 492.3; 378/65; 607/3; D24/158, 159, 202
See application file for complete search history.

(56) References Cited

U.S. PATENT DOCUMENTS

| 7,525,104 | B2 | 4/2009 | Harada | |
|---|---|---|---|---|
| 2005/0139787 | A1 | 6/2005 | Chiba et al. | |
| 2006/0118736 | A1* | 6/2006 | Moriyama et al. | 250/493.1 |
| 2006/0231775 | A1 | 10/2006 | Harada | |
| 2007/0131876 | A1 | 6/2007 | Brahme | |
| 2007/0295910 | A1 | 12/2007 | Harada | |
| 2008/0067401 | A1 | 3/2008 | Harada | |
| 2008/0258083 | A1 | 10/2008 | Naumann et al. | |
| 2009/0129545 | A1 | 5/2009 | Adler et al. | |
| 2009/0163799 | A1* | 6/2009 | Erbel et al. | 600/424 |
| 2009/0314960 | A1 | 12/2009 | Balakin | |
| 2010/0108903 | A1 | 5/2010 | Bert et al. | |
| 2010/0171047 | A1 | 7/2010 | Matsuda et al. | |
| 2010/0207042 | A1* | 8/2010 | Harada et al. | 250/492.3 |

(Continued)

FOREIGN PATENT DOCUMENTS

JP 11-297500 A 10/1999
JP 2006-288875 A 10/2006

(Continued)

OTHER PUBLICATIONS

International Search Report (PCT/ISA/210) issued on Oct. 12, 2010, by Japanese Patent Office as the International Searching Authority for International Application No. PCT/JP2010/065515.

(Continued)

*Primary Examiner* — Robert Kim
*Assistant Examiner* — Jason McCormack
(74) *Attorney, Agent, or Firm* — Buchanan Ingersoll & Rooney PC

(57) ABSTRACT

There are provided with a respiration induction apparatus that induces respiration, based on a desired respiration waveform; a switching device that switches the orbit of a particle beam; and an irradiation apparatus that controls irradiation, in synchronization with the desired respiration waveform. A controller, which performs synchronization control of the switching device and the respiration induction apparatuses in a plurality of treatment rooms, adjusts the periods and the phases of the desired respiration waveforms of the respiration induction apparatuses in the treatment rooms so that the irradiation times synchronized with the desired respiration waveforms in the treatment rooms do not overlap with one another, and controls the switching device so as to switch the orbits of the particle beam, in accordance with the respective irradiation times of the treatment rooms.

8 Claims, 5 Drawing Sheets

(56) References Cited

U.S. PATENT DOCUMENTS

| | | |
|---|---|---|
| 2010/0266100 A1 | 10/2010 | Balakin |
| 2011/0233423 A1 | 9/2011 | Balakin |

FOREIGN PATENT DOCUMENTS

| | | | |
|---|---|---|---|
| JP | 2010-063725 A | | 3/2010 |
| JP | 2010-094357 A | | 4/2010 |
| JP | 4531122 B2 | | 6/2010 |
| WO | WO 2006/082651 A1 | | 8/2006 |
| WO | WO 2009/150708 A1 | | 12/2009 |

OTHER PUBLICATIONS

Written Opinion (PCT/ISA/237) issued on Oct. 12, 2010, by Japanese Patent Office as the International Searching Authority for International Application No. PCT/JP2010/065515.

* cited by examiner

PARTICLE BEAM THERAPY SYSTEMS AND THE METHODS FOR TIME-SHARING IRRADIATION This application is a divisional of U.S. application Ser. No. 13/119,594 filed on Mar. 17, 2011 which is a U.S. national stage application based on International Application No. PCT/JP2010/065515 filed on Sep. 9, 2010, the entire contents of which is incorporated herein by reference.

TECHNICAL FIELD

The present invention relates to a particle beam therapy system, which is a medical system that performs therapy by irradiating a charged particle beam, including a heavy particle beam such as a carbon beam or a proton beam, onto the diseased site of a cancer or the like.

BACKGROUND ART

In the particle beam therapy, therapy is implemented by irradiating a charged particle beam (referred to as a particle beam, hereinafter) onto a diseased site, which is a therapy subject, so as to cause damage to diseased tissue; it is required to give a sufficient dose to the diseased tissue, which is an irradiation subject, and suppress a dose to the peripheral tissues. Accordingly, the irradiation dose and the irradiation coverage (referred to as an irradiation field, hereinafter) is controlled in accordance with the shape of the irradiation subject. With regard to an irradiation subject whose position and shape change with breathing, a respiratory phase is measured, and then a particle beam is irradiated onto the irradiation subject at a respiratory phase when the position and the shape are stabilized (for example, refer to Patent Documents 1 and 2).

Meanwhile, the plant of an accelerator, which is a beam supply source in particle beam therapy, is gigantic; therefore, in general, even at an institution having a plurality of treatment rooms, the courses of a particle beam outputted from a single accelerator are switched so that a particle beam is supplied to each treatment room. Accordingly, in order to enable a great number of patients to undergo the therapy, there have been proposed a particle beam therapy system in which the control of course-switching electromagnets is contrived in such a way that the time required to switch the courses of a particle beam is shortened (e.g., refer to Patent Document 3) and a particle beam therapy system in which the respiration is induced in such a way as to be in phase with the operation cycle of an accelerator or the like so that the therapy time is shortened (e.g., refer to Patent Document 4).

PRIOR ART REFERENCE

Patent Document

[Patent Document 1] Japanese Patent Application Laid-Open No. 2006-288875 (Paragraphs 0037 through 0040, FIGS. 7 through 9)

[Patent Document 2] International Publication No. WO2006/082651A1 (Paragraphs 0092 through 0096, FIG. 16)

[Patent Document 3] Japanese Patent Application Laid-Open No. 2010-63725 (Paragraph 0069, FIG. 3)

[Patent Document 4] International Publication No. WO2009/150708A1 (Paragraphs 0021 through 0026, FIGS. 1 and 6)

DISCLOSURE OF THE INVENTION

Problem(s) to be Solved by the Invention

However, in each of the foregoing particle beam therapy systems, among a plurality of treatment rooms, there exists a single treatment room for which the course of a particle beam is set and only in which therapy can be performed in a given time; in other treatment rooms, there is performed only waiting work such as preparation for therapy or putting the treatment room in order. Accordingly, even when the time for each process is shortened, limitation is imposed on increase in the number of patients who can be treated.

The present invention has been implemented in order to solve the foregoing problems; the objective thereof is to obtain a particle beam therapy system with which particle beam irradiation is implemented in a plurality of treatment rooms in the same time period so that a great number of patients can undergo the therapy.

Means for Solving the Problem

A particle beam therapy system according to the present invention is provided with a plurality of treatment rooms; a particle beam transport path that connects an accelerator with each of the plurality of treatment rooms; a switching device, provided in the transport path, that switches the orbits of a particle beam emitted from the accelerator, in such a way that the particle beam is supplied to one of the plurality of treatment rooms; a respiration induction apparatus, provided in each of the plurality of treatment rooms, that induces the respiration of a patient, based on a desired respiration waveform; an irradiation apparatus, provided in each of the plurality of treatment rooms, that forms a supplied particle beam into an irradiation field corresponding to an irradiation subject and controls irradiation onto the irradiation subject, in synchronization with at least the desired respiration waveform; and a controller that performs synchronization control of the switching device and the respiration induction apparatuses in a predetermined number of, at least two, treatment rooms among the plurality of treatment rooms. The particle beam therapy system is characterized in that the controller adjusts the periods and the phases of the desired respiration waveforms in the predetermined number of treatment rooms so that irradiation times synchronized with the desired respiration waveforms do not overlap with one another, and controls the beam orbit switching timing of the switching device so as to switch the orbits of the particle beam, in accordance with the respective irradiation times of the predetermined number of treatment rooms.

Advantage of the Invention

In a particle beam therapy system according to the present invention, a particle beam supplied from an accelerator is irradiated in a time-sharing manner in a plurality of treatment rooms within a respiration period, so that the particle beam can concurrently be irradiated in the plurality of treatment rooms. As a result, there can be obtained a particle beam therapy system that enables a great number of patients to undergo the therapy.

BEST MODE FOR CARRYING OUT THE INVENTION

Embodiment 1

Figure 1:
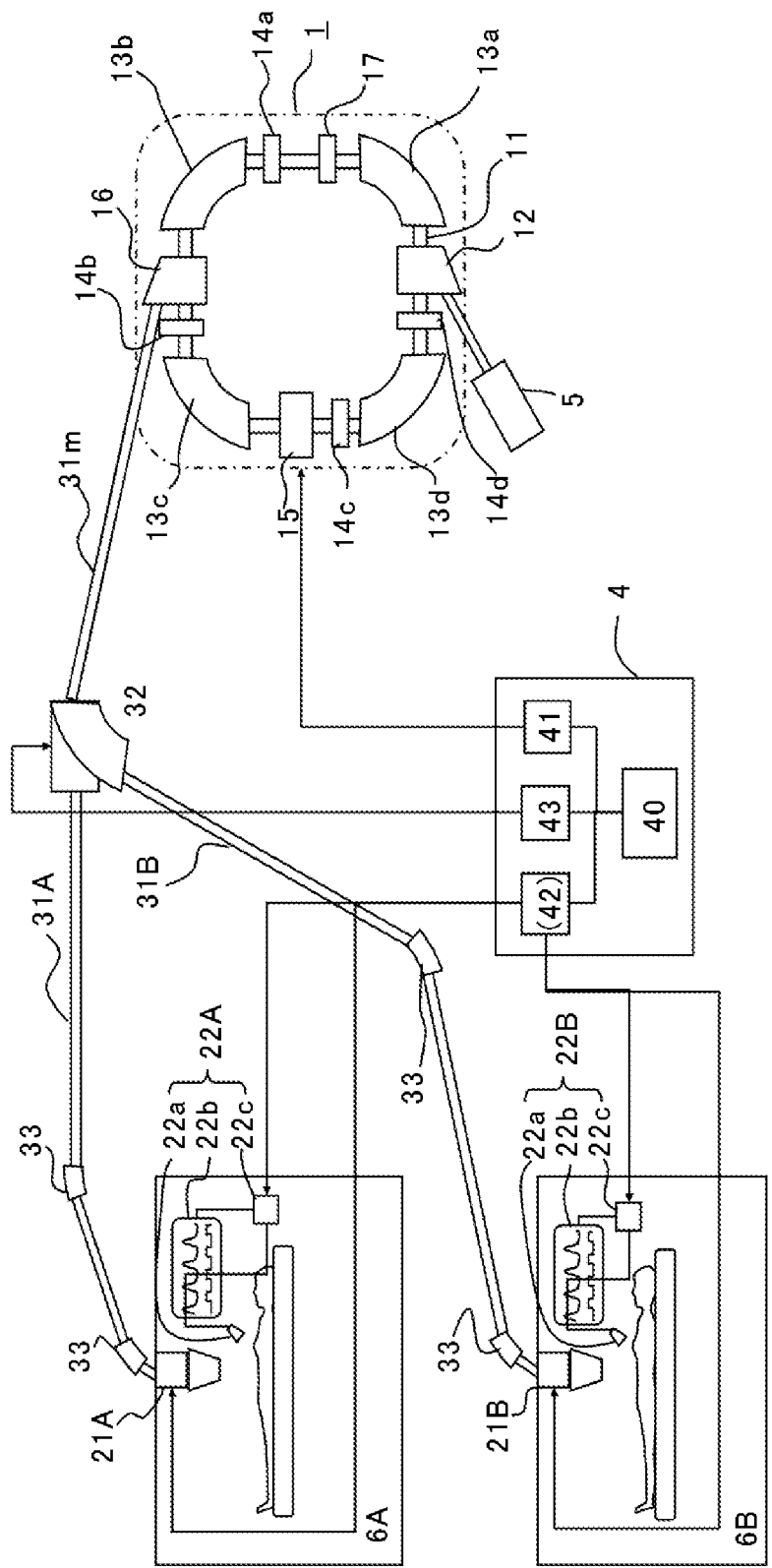
FIG. 1 is a diagram for explaining the overall configuration of a particle beam therapy system according to Embodiment 1 of the present invention.
Figure 2:
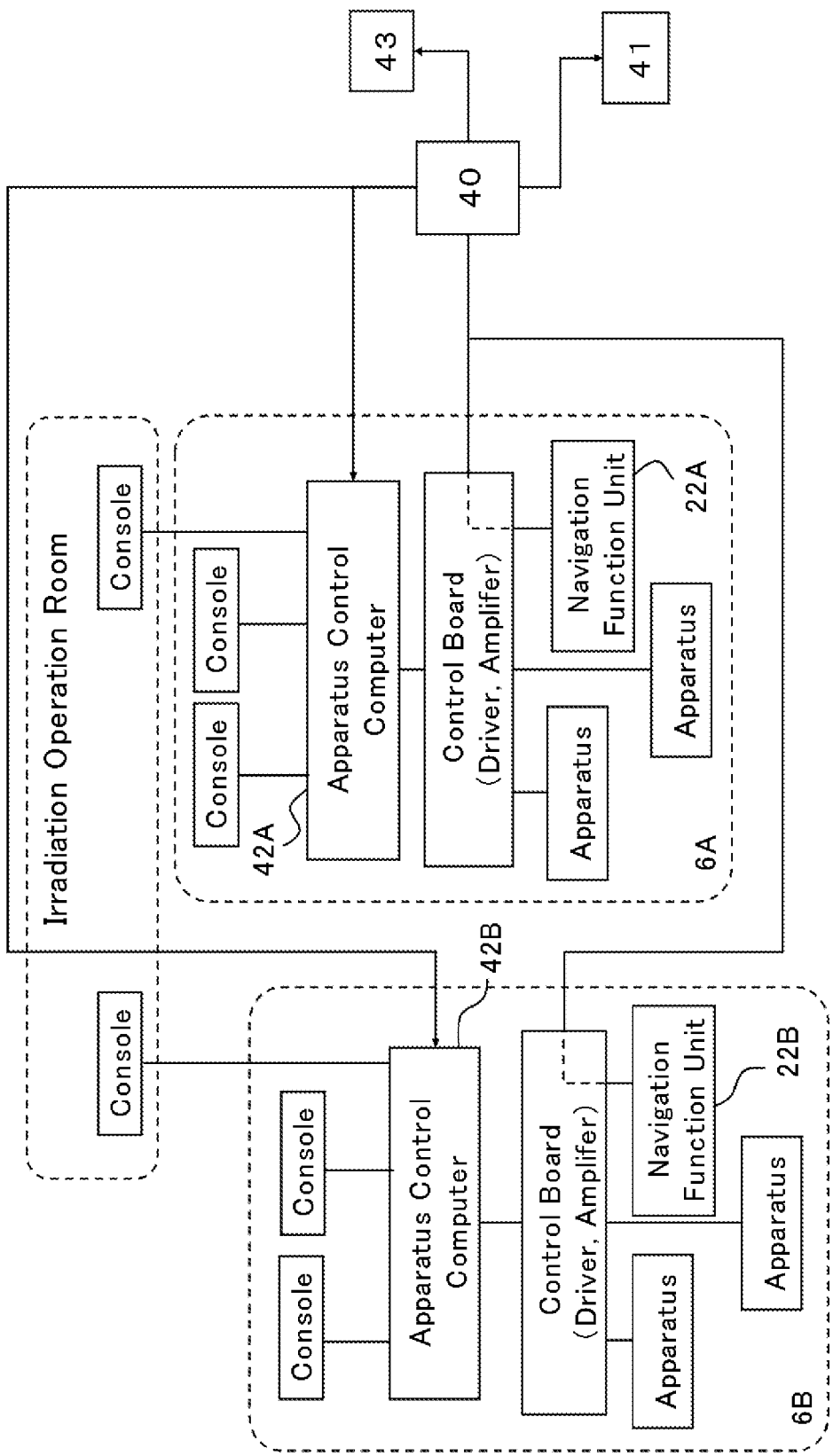
FIG. 2 is a functional block diagram for explaining the configuration of the control system in a particle beam therapy system according to Embodiment 1 of the present invention.
Figure 3:
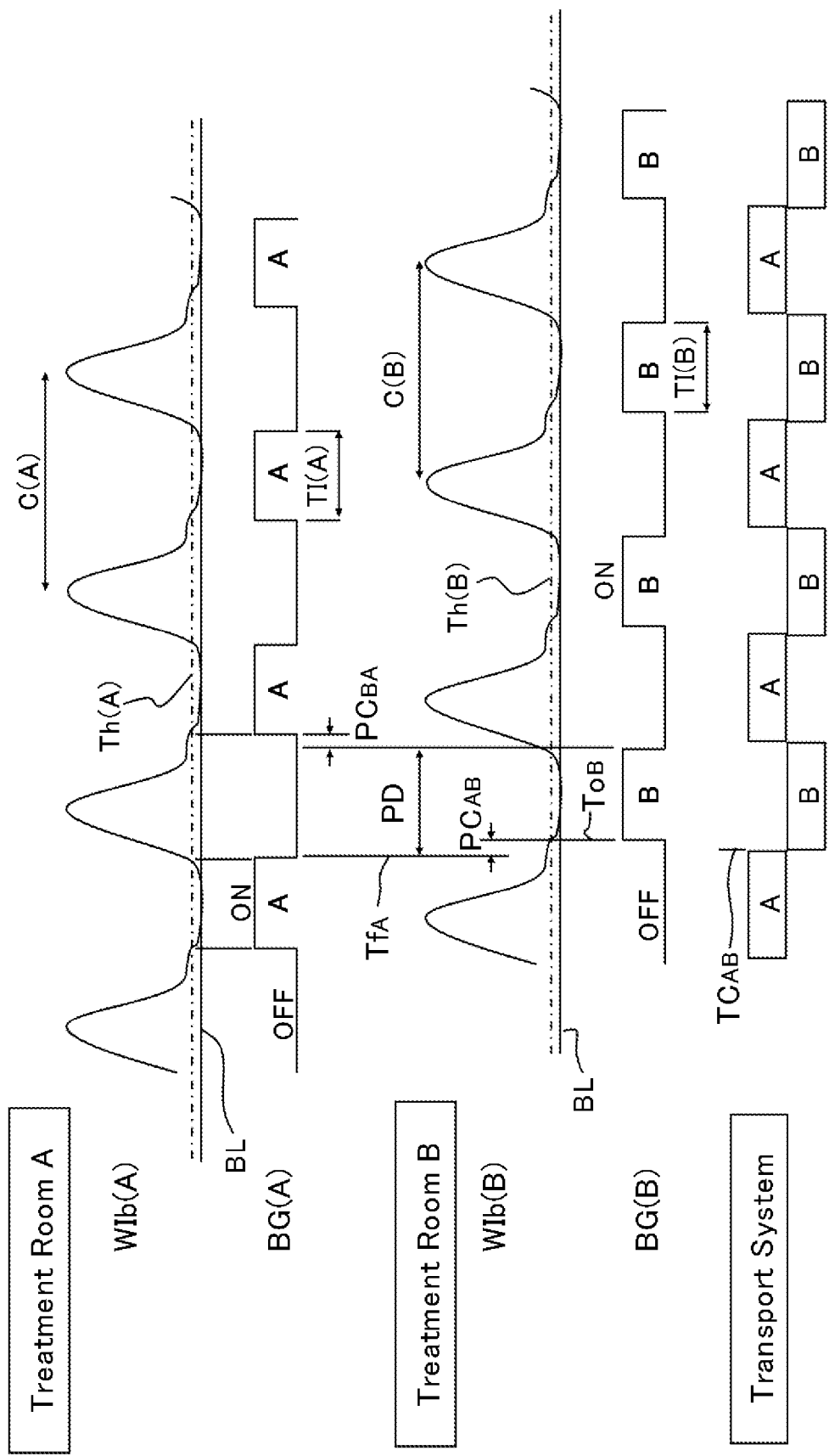
FIG. 3 is a set of timing charts for explaining cooperative control between a plurality of treatment rooms and the transport system in a particle beam therapy system according to Embodiment 1 of the present invention.
Figure 4:
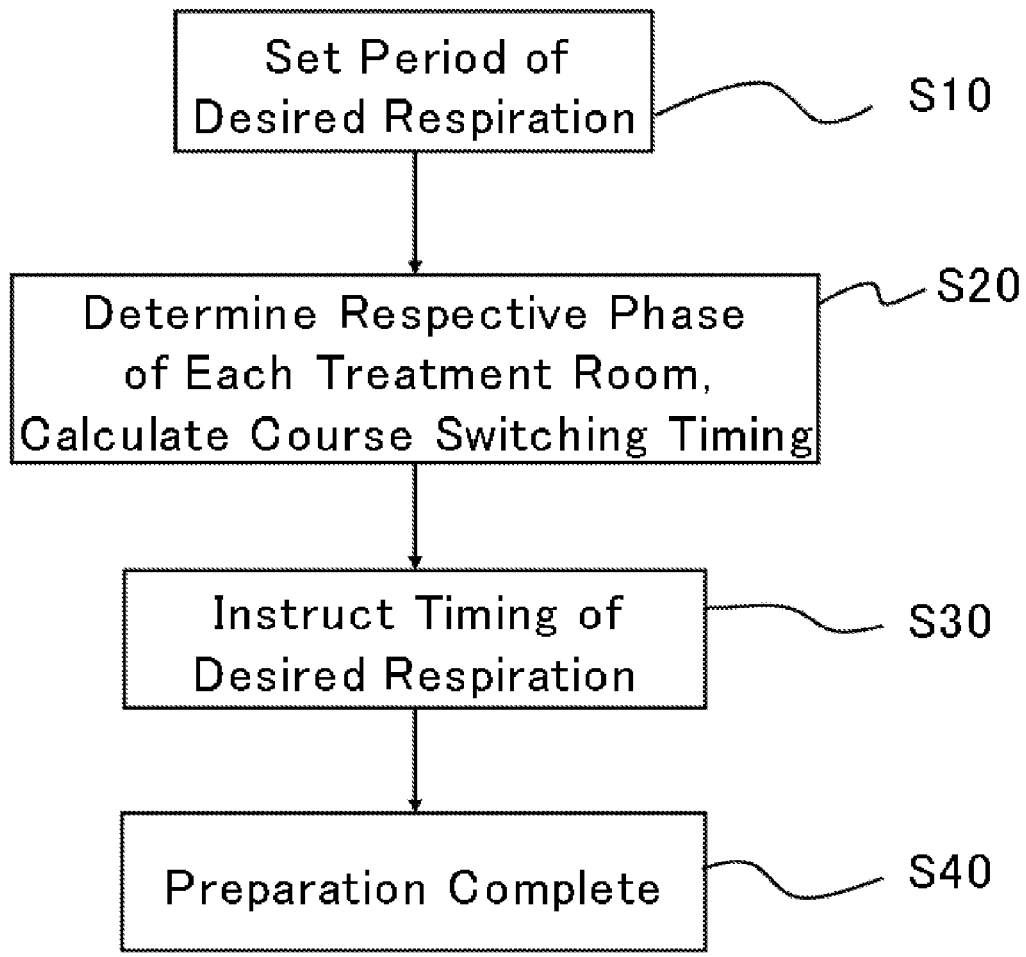
FIG. 4 is a flowchart for explaining the operation of a particle beam therapy system according to Embodiment 1 of the present invention.

The configuration of a particle beam therapy system according to Embodiment 1 of the present invention will be explained below. Each of FIG. 1 to FIG. 4 is a diagram, a chart, or a flowchart for explaining the configuration of a particle beam therapy system according to Embodiment 1 of the present invention; FIG. 1 is a diagram illustrating the configuration of a particle beam therapy system; FIG. 2 is a functional block diagram for explaining the configuration related to control of a particle beam therapy system; FIG. 3 is a set of charts representing the respiration navigation in each of treatment rooms and control timings in the transport system of a particle beam therapy system. FIG. 4 is a flowchart for explaining the operation of a particle beam therapy system.

At first, the configuration of a particle beam therapy system will be schematically explained with reference to FIG. 1. In FIG. 1, a particle beam therapy system is provided with a circular accelerator (just referred to as an accelerator, hereinafter) 1, which is a synchrotron as a supply source of a charged particle beam; an irradiation system 2 equipped with an irradiation apparatus provided in each of treatment rooms; a transport system 3 that connects the accelerator 1 with each treatment room and transports a charged particle beam from the accelerator to the irradiation apparatus in each treatment room; and a control system 4 that cooperatively controls these systems (subsystems, described later). The characteristic of the configuration of a particle beam therapy system according to Embodiment 1 of the present invention lies in the fact that the phase control of respiration induction in the irradiation apparatus of each treatment room is synchronized with the phase control of respiration induction in the irradiation apparatus of each other treatment room and with the course switching for the transport system. The cooperative operation through synchronization will be explained in detail later; thus, each configuration will be explained first.

<Accelerator>

The accelerator 1 is provided with a vacuum duct 11 that serves as an orbit path through which a charged particle beam circulates; an injector 12 for injecting a charged particle beam, supplied from a prestage accelerator 5, into the vacuum duct 11; deflection electromagnets 13a, 13b, 13c, and 13d (collectively referred to as 13) for deflecting the orbits of charged particles so that the charged particles form a charged particle beam that circulates along a circulation orbit in the vacuum duct 11; convergence electromagnets 14a, 14b, 14c, and 14d (collectively referred to as 14) for converging a charged particle beam formed on the circulation orbit not to diverge; a high-frequency wave acceleration cavity 15 that applies a high-frequency voltage, synchronized with circulating charged particles, to the circulating charged particles so as to accelerate the charged particles; an emission apparatus 16 for extracting from the accelerator 1 a charged particle beam accelerated in the accelerator 1 and emitting the extracted charged particle beam into the transport system 3; and a six-pole electromagnet 17 that excites resonance in the circulation orbit of a charged particle beam in order to make the emission apparatus 16 emit the charged particle beam.

There are provided unillustrated apparatuses for controlling the respective units; for example, in the deflection electromagnet 13, there is provided a deflection electromagnet control apparatus that controls the excitation current for the deflection electromagnet 13, and in the high-frequency wave acceleration cavity 15, there are provided a high-frequency wave source for supplying a high-frequency voltage to the high-frequency wave acceleration cavity 15 and a high-frequency wave control apparatus for controlling the high-frequency wave source; in the control unit 4, there is provided an accelerator control apparatus 41 that controls the whole accelerator 1 by controlling other components such as the deflection electromagnet control apparatus, the high-frequency wave control apparatus, and convergence electromagnet 14.

However, in the technical idea of the present invention, the control of the accelerator 1 itself is not limited; therefore, the accelerator is not limited to the one having the foregoing configuration, and it goes without saying that various modifications are allowed, as long as the variants can stably emit a charged particle beam into the transport system 3.

Figure 5:
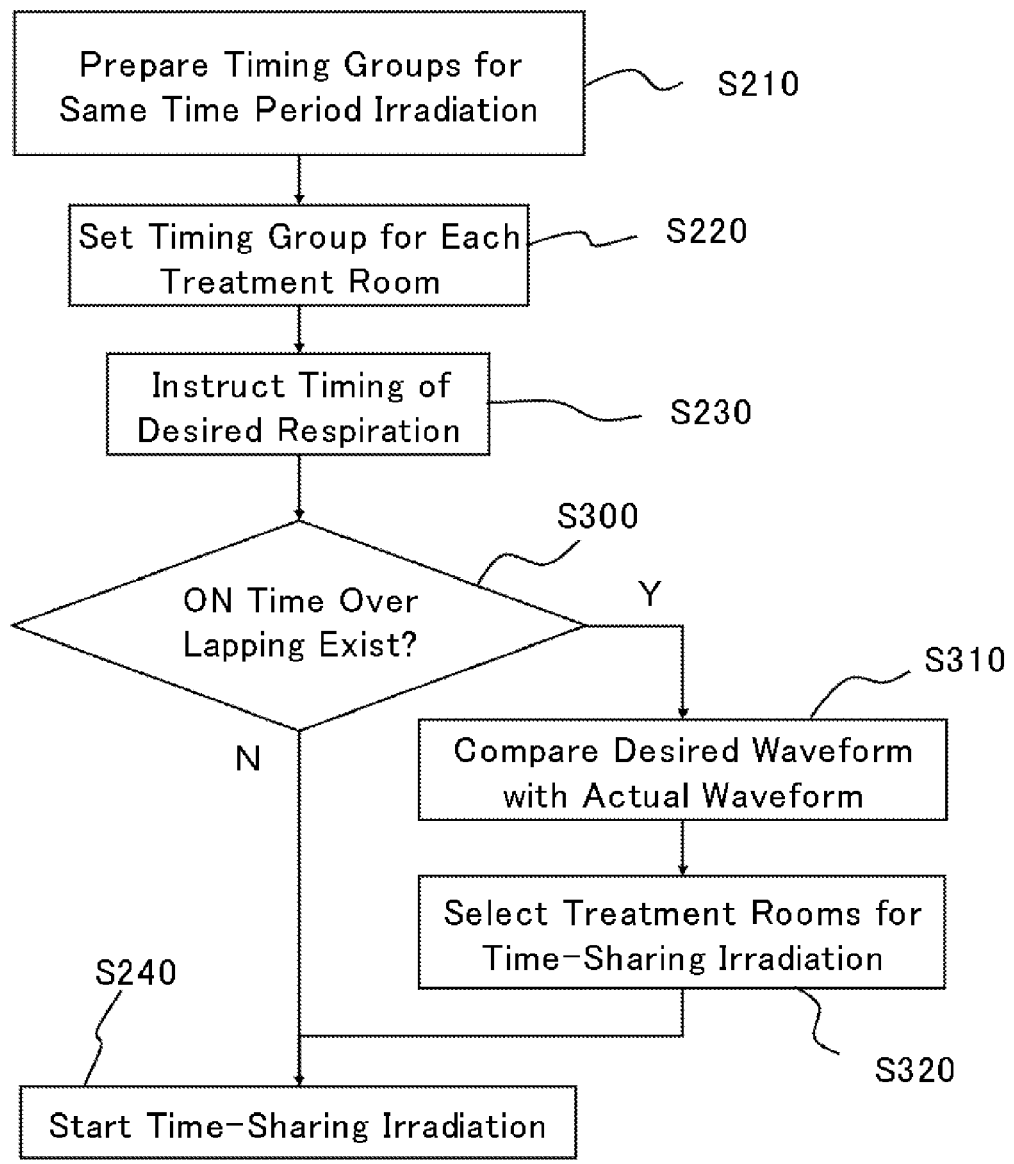
FIG. 5 is a flowchart for explaining the operation of a particle beam therapy system according to Embodiment 2 of the present invention.

In FIG. 5, for the sake of simplicity, the prestage accelerator 5 is illustrated as if it is a single apparatus; however, in practice, the prestage accelerator 5 includes an ion source (ion beam generator) that generates a charged particle (ion) such as a proton or a carbon particle (heavy particle) and a linear accelerator system that performs initial acceleration of a generated charged particle. A charged particle injected from the prestage accelerator 5 to the accelerator 1 is accelerated in a high-frequency electric field up to 70% to 80% of the light velocity, as it is being bent by means of the magnets.

<Transport System>

The charged particle beam accelerated by the accelerator 1 is emitted to the transport system 3, which is referred to as an HEBT (High Energy Beam Transport) system. The transport system 3 is provided with a vacuum duct (a main duct 31m, a treatment-room-A duct 31A, and a treatment-room-B duct 31B: collectively referred to as a vacuum duct 31); a switching electromagnet 32, which is a switching device for switching the orbit of a charged particle beam; and a deflection electromagnet 33 that deflects a beam at a predetermined angle. The charged particle beam that has been sufficiently energized by the accelerator 1 and travels through the transport path formed of the vacuum duct 31 is led to the irradiation apparatus provided in a designated treatment room; changing the orbit of the charged particle beam (to the 31A direction or to the 31B direction) with the switching electromagnet 32, as may be necessary.

<Irradiation System>

The irradiation system 2 includes an irradiation apparatus 21 that forms a charged particle beam supplied from the transport system 3 into an irradiation field conforming to the size or the depth of a diseased site of a patient as an irradiation subject and a navigation function unit 22 having a respiratory navigation function of inducing respiration at a time when irradiation is performed. In conjunction with at least respiratory navigation, the on/off of irradiation onto a diseased site as an irradiation subject is controlled in accordance with the phase in the period of a desired respiration waveform utilized in the respiratory navigation. As described "the irradiation apparatus provided in a designated treatment room" in the explanation for the transport system, a particle beam therapy system, in general, is provided with a plurality of treatment rooms (treatment rooms 6A and 6B in FIG. 1, are collectively referred to as a treatment room 6) in view of the therapy efficiency. In other words, in the irradiation system 2, the irradiation apparatus 21 and the navigation function unit 22 are provided in each treatment room 6; for example, an irradiation system 2A for the treatment room 6A includes an irradiation apparatus 21A and a navigation function unit 22A.

In order to realize the respiratory navigation function, the navigation function unit 22 is provided with a patient respiration measurement apparatus 22a for measuring the respiratory state of a patient; a respiration synchronization apparatus 22c that permits particle beam irradiation onto a patient, based on measurement information from patient respiration measurement apparatus 22a; and a respiration information instruction apparatus 22b for giving instructions to a patient about information on respiration synchronization.

<Control System>

In many cases, a control system for such a large-size complex system configured with a plurality of subsystems, in general, includes a sub-controller that is dedicated to control of each subsystem and a main controller that conducts and controls the whole system. This configuration with a main controller and a sub-controller is adopted also in the control system 4 for a particle beam therapy system according to Embodiment 1 of the present invention. For the sake of simplicity, there will be explained a control system, among control systems for a particle beam therapy system, which relates to the control of three subsystems, i.e., the accelerator 1, the transport system 3, and the irradiation system 2; in other words, there will be explained the control system 4 provided with an accelerator control unit 41, a transport system control unit 43, an irradiation system control unit 42, and a whole system control unit 40, as illustrated in FIG. 1.

The control system 4 will be explained with reference to FIG. 2, which schematically illustrates the configuration of the control system. Meanwhile, in general, as the controller of a particle beam therapy system, a workstation or a computer is utilized. Accordingly, in many cases, the controller is referred to as a "computer". For example, the main controller 40 in FIG. 2 is, in fact, a function of a computer, which is, in many cases, referred to as an irradiation system common computer; however, the main controller 40 is dealt with as a controller having a specific function. The apparatus control computer corresponds to a sub-controller 42 that controls the irradiation system 2, which is a subsystem; the portions thereof corresponding to the respective controllers for the irradiation systems 2A and 2B that are separately arranged in the treatment rooms 6A and 6B are designated as 42A and 42B, respectively. As described above, the particle beam therapy system 4 is provided with the main controller 40 and the sub-controllers 41, 42, and 43, which are controllers for the accelerator 1, the irradiation system 2, and the transport system 3, respectively. The sub-controllers 41, 42, and 43 perform control operations in a collaborative manner, based on a timing instruction function provided in the main controller 40. The timing instruction function itself may be the one, described in Patent Document 3, for example, that outputs a timing signal for synchronization. The respective positions and the like of the sub-controllers in FIGS. 1 and 2 differ from each other; this is because the sub-controllers are collectively illustrated as a composition of the controller 4 in FIG. 1, on the other hand, the sub-controller are illustrated with respect to the control subjects in FIG. 2; thus, that does not represent the matter as to whether or not the physical positions are different from each other. In other words, it is not substantial matter how physically arranged the sub-controllers are.

The respective "consoles" connected with the apparatus control computers (the sub-controllers 42A and 42B) are each a keyboard, a display, or the like or a terminal such as a controller box; in other words, it is a man-machine interface. Consoles are set in the treatment room 6 and an irradiation operation room that is provided separately from the treatment room, in many cases. A control board is connected at a lower hierarchical level than the apparatus control computer is connected. Specifically, as described in parentheses, the control boards is the driver, the amplifier, the PLC (Programmable Logic Controller), or the like for each of the apparatuses. Apparatuses are connected at a further lower hierarchical level than the control board is connected. The apparatuses include a motor for moving the respective axes of a treatment table, a motor for driving the X-ray image-capturing device in the irradiation apparatus, and the like; in general, the irradiation apparatus 21 and the navigation function unit 22, described above, are also included.

However, it is described that in the case of the particle beam therapy system according to Embodiment 1, the navigation function unit 22 is directly controlled by the main controller 40, without involving the control board provided in the treatment room 6. The reason for this is that because, as described later, in the particle beam therapy system according to Embodiment 1, it is required to control the respiratory navigation not discretely in a single treatment room but collaboratively with other treatment rooms and the transport system, the number of the apparatuses involved is reduced as much as possible so that the occurrence of wasteful time (delay) is prevented from shifting the timing. In this regard, however, the direct connection is not the indispensable condition; it goes without saying that the way of connection may appropriately be changed as long as the timing can be ensured.

The other role of the navigation function unit and irradiation system common computer (main controller 40) is to conduct the whole particle beam therapy system; in some cases, as the controller for an apparatus that requires control synchronizes with the accelerator 1 and the transport system 3, the irradiation system common computer undertakes some of the functions of the sub-controller 42. That is why in FIG. 1, reference numeral 42 is in parentheses.

As described above, the control function related to the navigation function unit 22 among the control functions of the sub-controller 42 is undertaken by the main controller 40. The apparatuses such as a motor for moving the respective axes of a treatment table and a motor for driving the X-ray image-capturing device in the irradiation apparatus are controlled by intermediary of the sub-controller 42, as usual. The motor for the treatment table and the motor for the X-ray image-capturing device are not moved when a beam is being irradiated. That is to say, this is because it is not required to implement control in synchronization with the accelerator system 1 and the transport system 3. In order to exchange information about their conditions, the irradiation system common computer (main controller 40) and the irradiation system apparatus control computer (sub-controller 42) communicate with each other, for example, by use of a Ready signal that indicates in which treatment room 6 the irradiation system 2 has completed its positioning and is ready to irradiate a beam, a signal that indicates in which treatment room 6 the irradiation system 2 has irradiated a beam and completed its irradiation. Briefly speaking, it is regarded as carrying out events sequentially. In other words, in terms of relationship with the sub-controller 42, the role of the irradiation system common computer (main controller 40) is to perform irradiation management with regard to, for example, "which irradiation systems 2 in the respective treatment rooms 6 contend with one another for a beam from the accelerator"; once it is determined which irradiation systems 2 in the respective treatment rooms 6 contend with one another for a beam from the accelerator, the sub-controller 42 in each treatment room 6 can determine the sequence.

However, as described later, in the particle beam therapy system according to Embodiment 1 of the present invention, it is required to control respiration in each treatment room and beam switching synchronously. In other words, the sequence cannot be determined only by the sub-controller in each treatment room. Therefore, the command value to the navigation function unit 22 is transmitted not from the apparatus control computer (sub-controller 42) but from the irradiation system common computer (main controller 40) directly.

Meanwhile, among the functions of the irradiation system 2, the function of forming an irradiation field is not the essential part of the present invention. Accordingly, the description about the configuration of the irradiation apparatus 21 will be omitted. In contrast, the beam gate, which on/off-controls the irradiation onto an irradiation subject in conjunction with the respiration navigation, requires synchronization with the transport system 3; therefore, although not illustrated in FIG. 2, the beam gate is directly controlled by the main controller 40. Furthermore, the wobbler electromagnet or the scanning electromagnet, which requires the control synchronized with the accelerator system 1, is also an apparatus included in the irradiation apparatus 21; thus, for the same reason, the wobbler electromagnet or the scanning electromagnet is directly controlled by the irradiation system common computer 40.

Next, with reference to FIG. 3, there will be explained a method in which in the particle beam therapy system according to Embodiment 1 of the present invention, in order to irradiate a particle beam supplied from the accelerator 1 simultaneously in a plurality of treatment rooms in a time-sharing manner, the respiration navigation is controlled in a cooperative manner. In FIG. 3, the top chart represents a respiration navigation waveform WIb(A), and a threshold value Th(A) and a beam gate on/off signal BG(A) for WIb(A) in the treatment room 6A; the intermediate chart represents a respiration navigation waveform WIb(B), and a threshold value Th(B) and a beam gate on/off signal BG(B) for WIb(B) in the treatment room 6B; BL denotes the base line. The bottom chart represents the beam orbits (courses) that are witched by the beam switching electromagnet 32 in the transport system 3. In FIG. 3, the abscissas, which are common (synchronized with one another) in all the charts, are each the duration corresponding to several times as long as the respiration period; as a position on the abscissa moves rightward, the time advances. In the case of the respiration navigation waveform (WIb(A) and WIb(B) are collectively referred to as WIb, and Th(A) and Th(B) are collectively referred to as Th), the ordinate represents the state of respiration; the waveform moving upward suggests an inhaling state, and the waveform moving downward suggests an exhaling state. In the case of the beam gate on/off signal (BG(A) and BG(B) are collectively referred to as BG), the upper portion thereof suggests an on state, and the lower portion suggests an off state; in the case of the orbit, the upper portion suggests that the orbit (course) is set in such a way that a beam advances to the treatment room 6A, and the lower portion suggests that the orbit is set in such a way that a beam advances to the treatment room 6B.

In the respiration information instruction apparatus 22b provided in each treatment room 6, the navigation waveform (desired respiration wave) in FIG. 3 is displayed in such a way as to be scrolled from right to left as the time elapses; the respiration of a patient is navigated through the display of the desired respiration waveform to be scrolled. In this situation, in the case where as the respiration measurement apparatus 22a, for example, there is utilized a laser displacement gauge for measuring the abdominal movement of a patient and as the display unit for the ordinate, an output amount of the laser displacement gauge is utilized, the respiration can be navigated while the difference from the navigation is visually shown to the patient, by displaying an actual measurement value superimposed on the desired respiration wave.

In general, the position of the diseased organ of a patient is stabilized most when the respiration is in the exhaling state (the lower portion with respect to the ordinate); therefore, the treatment is planed, based on the position or the shape of an irradiation subject at a time the respiration is in the exhaling state, and irradiation is implemented when the respiration is in the exhaling state. The threshold value Th in FIG. 3 denotes a value that serves as a reference for permitting beam irradiation. The respiration gate signal BG becomes ON when the desired respiration waveform WIb becomes lower than the threshold value Th. In treatment, when both the desired respiration waveform and an unrepresented waveform indicating the actual exhaling state are the same as or smaller than the threshold value, irradiation is permitted. In this specification, for the purpose of simplifying the explanation for the synchronized control, there will be omitted the explanation for the control based on the waveform indicating the actual exhaling state.

Here, there will be described the course switching in the transport system. In a conventional particle beam therapy system, once therapy is started in one of the treatment rooms, the course is not switched to another treatment room halfway through the therapy, until the therapy is completed; therefore, unlike the bottom chart in FIG. 3, the course switching in the transport system is not performed during a single respiration period. In other words, until irradiation onto one patient is completed, irradiation onto another patient is not implemented. Also in the particle beam therapy system according to Embodiment 1, a charged particle beam supplied from the accelerator 1 is shared with time; thus, the respiration gates of the treatment rooms 6A and 6B do not concurrently turn on. However, in the particle beam therapy system according to Embodiment 1, by performing switching between the course for the treatment room 6A and the course for the treatment room 6B twice or more times (every respiration period) during a single irradiation, it is made possible to irradiate a particle beam onto a plurality of patients in the same time period, i.e., it is made possible to make the plurality of patients undergo particle beam therapy. The method of realizing it will be explained in detail below.

In general, the period of human respiration is not constant, and the length of the respiration depends on individuals. However, by means of a respiratory navigation apparatus or the like, it is possible to induce respiration in such a way as to have a constant period. This is because although respiration is controlled by autonomic nerves, it is exceptionally possible to consciously perform respiration. Accordingly, in Patent Document 4, respiratory navigation is performed with a period suitable for the period of an accelerator. However, even in that case, while irradiation is carried out in one treatment room, no irradiation is implemented in another treatment room. Accordingly, in the particle beam therapy system according to Embodiment 1 of the present invention, the desired-respiration periods in the treatment rooms 6A and 6B are made to be the same as each other but shifted from each other by a predetermined amount, and the switching between the transport course to the treatment room 6A and the transport course to the treatment room 6B is performed at predetermined phases during the period, so that particle beam therapy can be provided in both the treatment rooms 6A and 6B during the same time period. It is made possible to set the period to an interval from 2 to 20 seconds, which is regarded as the average human respiration period; therefore, the shift of the phase can be adjusted in order to prevent the respiration gates for the treatment rooms 6A and 6B from turning ON at the same time. Explanation will be made below with reference also to the flowchart in FIG. 4.

The period of the desired respiration is set to the one suitable for patients who concurrently undergo the therapy. When the set period is inputted to the main controller 40, the main controller 40 determines the respective phases (shifts) of the treatment rooms and calculates the course switching timings Tc, in the transport system 3, corresponding to the shifted phases (the step S20). Then, a timing instruction apparatus included in the main controller 40 issues the following instructions. The timing instruction apparatus instructs the timings of desired respirations, whose timings are shifted from each other, to the respiratory navigation apparatuses 22A and 22B of the treatment rooms 6A and 6B. After that, the timing instruction apparatus instructs the timings to a course switching apparatus (the controller for the switching electromagnet 32 or the sub-controller 43 in FIG. 1) so that irradiation can be implemented in the treatment room A when the respiration gate for the treatment room A is ON and irradiation can be implemented in the treatment room B when the respiration gate for the treatment room B is ON (the step S30). As a result, when the preparation is completed in each treatment room, irradiation of a particle beam can be implemented concurrently in the treatment rooms 6A and 6B in a single time period (the step S40).

In this situation, the irradiation starting times of the two treatment rooms need not to be necessarily coincide with each other; both the irradiation starting time and the irradiation ending time may be determined for each treatment room. In this regard, however, when in the therapy in each treatment room, irradiation is implemented only at a predetermined phase of respiratory navigation, even in the case where the irradiation time periods of a plurality of treatment rooms (6A, 6B) overlap with one another, therapy in each treatment room can be implemented as if the therapy is implemented only in the independent treatment room, because a particle beam from the accelerator 1 is utilized in a time-sharing manner in a respiratory period.

In FIG. 3, for example, letting $TC_{AB}$ denote the timing when the course is switched from the treatment room 6A to the treatment room 6B, letting $Tf_A$ denote the timing when the gate for the treatment room 6A is switched from ON to OFF, and letting $TO_B$ denote the timing when the gate for the treatment room 6B is switched from OFF to ON, and, although not represented in FIG. 3, letting $TC_{BA}$ denote the timing when the course is switched from the treatment room 6B to the treatment room 6A, letting $Tf_B$ denote the timing when the gate for the treatment room 6B is switched from ON to OFF, and letting $TO_A$ denote the timing when the gate for the treatment room 6A is switched from OFF to ON, it is desirable to set the timing TC of switching the course in such a way that the following equations (1) and (2) are satisfied.

$$TC_{AB}-Tf_A<To_B-TC_{AB} \quad (1)$$

$$TC_{BA}-Tf_B<To_A-TC_{BA} \quad (2)$$

This is because with regard to the times $PC_{AB}$ (=$TO_B-Tf_A$) and $PC_{BA}$ (=$TO_A-Tf_B$) in which the gates for the two treatment rooms are both OFF, "the duration between a time point when the course is switched and a time point when the gate becomes ON" is made longer than "the duration between a time point when the gate becomes OFF and the time point when the course is switched" so that there can be ensured to have a time period from a time point when the course is switched to a time point when the orbit has been stabilized, in the case where the course switching electromagnet 32 in the transport system 3 is operated, Next, a method of forming the desired respiration waveform will be explained. The desired respiration waveform may be created artificially; however, it is the most natural to synchronize the respiration of a patient with the desired respiration waveform created from his own respiration waveform. The purpose of displaying a desired respiration waveform and synchronizing the respiration with the desired respiration waveform is to make the position-posture of a diseased site at a time when the treatment plan is created and those at a time when the therapy is implemented to be reproduced in such a way as to be the same as each other. Accordingly, at first, the patient is requested to respire in a comfortable position, and then the respiration is measured with the respiration measurement apparatus 22a. Next, by applying trimming, time expansion/contraction, averaging, or the like to the measured respiration waveform, there is set an appropriate period for making the period for the treatment room 6A and the period for the treatment room 6B to be the same as each other. In this situation, in the case where a natural respiration waveform of the patient is recorded in an unillustrated treatment planning apparatus, the optimum period of the desired respiration may be calculated from the recorded waveform. In addition, in selecting patients who concurrently undergo therapy, it may be allowed to automatically select patients, the natural-respiration periods of whom are close to one another, i.e., the periods of whom can readily be synchronized with one another.

In the foregoing explanation, adjustment has been made in such a way that the irradiations in two treatment rooms are performed in the same period but at the different phases; however, the adjustment is not limited to the above, for example, it is possible to adjust in such a way that even though the periods are in the integer-fold relationship, the irradiation times do not overlap with each other; thus, the periods of the irradiations are not limited to the same period, and it may be allowed that by adjusting both the period and the phase, the irradiation times are prevented from overlapping with each other.

As described above, the particle beam therapy system according to Embodiment 1 includes a plurality of treatment rooms 6; a navigation function unit 22, provided in each of the plurality of treatment rooms 6, that is a respiration induction apparatus for inducting the respiration of a patient, based on a desired respiration waveform WIb; a particle beam transport path 31 that connects an accelerator 1 with each of the plurality of treatment rooms 6; a switching electromagnet 32, provided in the transport path 31, that is a switching device for switching the orbits of a particle beam emitted from the accelerator 1, in such a way that the particle beam is supplied to one of the plurality of treatment rooms 6; an irradiation apparatus 21, provided in each of the plurality of treatment rooms 6, that forms a supplied particle beam into an irradiation field corresponding to an irradiation subject and controls irradiation onto the irradiation subject, in synchronization with at least the desired respiration waveform WIb; and a controller 4 that performs synchronization control of the switching electromagnet 32 and the respiration induction apparatuses 22 in a predetermined number of, at least two, treatment rooms 6A and 6B among the plurality of treatment rooms 6. The controller 4 adjusts the periods and the phases of desired respiration waveforms WIb(A) and WIb(B) for the respiration induction apparatuses 22 in a predetermined number of treatment rooms 6A and 6B so that the irradiation times (TI(A) and TI(B)) synchronized with the desired respiration waveforms WIb in the predetermined number of treatment rooms 6A and 6B do not overlap with each other, and controls the switching timing $TC_{AB}$ of the switching electromagnet 32 so as to switch the orbits of a particle beam, in accordance with the respective irradiation times (TI(A) and TI(B)) of the predetermined number of treatment rooms; therefore, a particle beam emitted from the accelerator 1 is supplied in a time-sharing manner to the plurality of treatment rooms in the respiration period, so that the particle beam can concurrently be irradiated. As a result, there can be obtained a particle beam therapy system in which particle beam irradiation is implemented in a plurality of treatment rooms in the same time period so that a great number of patients can undergo the therapy.

In particular, the controller 4 is configured to make adjustment in such a way that the desired respiration waveforms for the respiration induction apparatuses in a predetermined number of treatment rooms are created in the same period but at the different phases; therefore, adjustment can be implemented in such a way that irradiation times do not readily overlap with one another.

In particular, letting $TC_{12}$ denote the switching timing when the orbit is switched from the first treatment room (e.g., 6A) to the second treatment room (e.g., 6B), among the predetermined number of treatment rooms, letting $Tf_1$ denote the timing when irradiation in the first treatment room 6A is turned from ON to OFF, i.e., the irradiation is stopped, and letting $To_2$ denote the timing when irradiation in the second treatment room 6B is turned from OFF to ON, i.e., the irradiation is started, the controller 4 is configured to control the switching timings in such a way that the equation $[TC_{12}-Tf_1 < To_2-TC_{12}]$ is satisfied; therefore, when the course switching electromagnet 32 in the transport system 3 is operated, a time period from a time point when the course (orbit) is switched to a time point when the orbit has been stabilized becomes longer, whereby irradiation can stably be performed.

Embodiment 2

In Embodiment 1, there has been described a case where there exist two treatment rooms. However, in general, particle beam therapy systems often include three to four treatment rooms for a single main accelerator 1. Accordingly, in Embodiment 2, there will be explained a case where there exist three or more treatment rooms.

The following terms can be applied also to Embodiment 1; however, in explaining phase shifts among a great number of treatment rooms, several terms will be defined again.

<Respiration Period>

As represented in FIG. 3, the desired respiration waveform is formed of a waveform that periodically repeats the same pattern. For example, the local maximum point that indicates a state of inhaling most appears every constant time period. This constant time period is referred to as a "respiration period" (C(A) or C(B), collectively referred to as "C" in units of [sec]).

<Respiratory Phase>

As represented in FIG. 3, the desired respiration waveforms WIb(A) and WIb(B) are the same as each other in terms of the respiration period C but are different from each other in terms of the position of the local maximum point. The time difference between the same waveforms that overlap each other is referred to as a "phase difference". This phase difference may be considered in the same manner as a trigonometric function (sine, cosine) is considered. Accordingly, the unit for the phase is a radian or a degree (°).

<Duty Ratio>

As represented in FIG. 3, the respiration gate signal BG is determined in accordance with the desired respiration waveform WIb. In Embodiment 1, there has been explained a method in which the respiration gate signal BG becomes ON when the desired respiration waveform WIb becomes lower than the threshold value Th. As described above, the respiration gate signal BG is a PWM (Pulse Width Modulation)-like signal in which two value signals, i.e., ON and OFF, whose widths (durations) are adjusted, are repeated. The ratio of ON duration of the respiration gate signal to the OFF duration thereof can be expressed by a duty ratio. Specifically, the duty ratio is defined by the proportion of ON duration to the total period. For example, when the ratio of ON duration to OFF duration is 1 to 3, the duty ratio is 0.25 (=1/(1+3)).

Now, it is assumed that the respiration gate signal BG whose duty ratio is 0.5 (½) and repeating ON/OFF. In this case, if the phase is shifted by 180°, the gate signals BG for two treatment rooms can be prevented from becoming ON concurrently. That is to say, in the foregoing case, the maximum number of treatment rooms in which a beam can concurrently be irradiated in a time-sharing manner is "2". Ideally, when the duty ratio is 0.5, time-sharing concurrent irradiation can be performed in two treatment rooms. However, in practice, it is required to consider the time of switching courses for the treatment rooms, as well; therefore, there exists further restriction.

Meanwhile, considering the relationship between the respiration of a patient and the position-posture of a diseased organ, the following thing can be stated. As the threshold value Th is lower, the position-posture of a diseased site can be reproduced better. However, as the threshold value Th is made lower, the duty ratio of the respiration gate signal becomes smaller.

Accordingly, with reference to the flowchart in FIG. 5, there will be explained a time-sharing method for a case where there exist three or more treatment rooms. As a basis of consideration, it is assumed that the present case is a case where the duty ratio of the respiration gate signal BG corresponding to the desired respiration waveform WIb is slightly smaller than 0.5 (½), and although irradiation can be performed in the same time period in two treatment rooms, irradiation cannot be performed in the same time period in three treatment rooms, i.e., there exist treatment rooms, the irradiation ON durations for which overlap with each other. In addition, it is assumed that there are prepared two timing groups α and β having, as the desired respiration waveform WIb, the waveform WIb(α) and the waveform WIb(β), respectively, whose phases are different from each other by 180° (the step S210).

At first, display is performed through the console of the irradiation system common computer (main controller 40) so that a doctor or the like who intends to start therapy in one (e.g., 6A) of the treatment rooms 6A through 6C can ascertain the therapy situation of other treatment rooms (e.g., 6B and 6C). Here, the therapy situation signifies whether or not therapy is performed and which desired respiration waveform (α or β) is selected. Next, the result of the selection, managed by the irradiation system common computer (main controller), between α and β of the timing groups for the desired respiration waveform is inputted by the doctor or the like in accordance with the therapy situation of other treatment rooms, and then the timing group is set to the inputted group (the step S220). That is to say, the group (the group α or the group β) to which each of the treatment rooms belongs is selected. It may also be allowed that in the step S220, display is not provided to the doctor or the like and the controller corresponding to each treatment room determines so as to appropriately select the group. Alternatively, each treatment room may preliminarily be categorized to the group α or the group β.

To the treatment room (the sub-controller 42 or the navigation function unit 22 thereof) that is categorized to a group, the main controller 40 outputs a timing signal corresponding to the group (the step S230). When the timing signal is inputted, the desired respiration waveform WIb corresponding to the selected group is displayed in each treatment room.

When the desired respiration waveform WIb is displayed, the patient gradually steadies his breath in synchronization with the desired respiration waveform WIb. In this situation, in the case where any one of the groups α and β is not selected in a plurality of treatment rooms, i.e., in the case where there exist no treatment room, the ON time period for which overlaps with one for another (determined as "N" in the step S300), time-sharing irradiation can be started, as is the case with the step S40 in Embodiment 1 (the step S240). However, in the case where as stated in the precondition, a plurality of treatment rooms selects the same group, the ON time periods of the treatment rooms that select the same group overlap with one another. In that case (determined as "Y" in the step S300), the treatment rooms in which time-sharing irradiation is to be performed are narrowed down as follows.

The main controller 40 having the timing instruction apparatus compares the respective desired respiration waveforms for at least the treatment rooms that have selected the same group with the actual respiration waveform outputted from the patient respiration measurement apparatus 22a (the step S310). After that, based on the result of the comparison, the irradiation preparation degree of each treatment room is scored; in the case where the score of a given treatment room is larger than a predetermined value, it is determined that irradiation can be performed, and then the treatment room is determined as the one in which time-sharing irradiation is to be performed (the step S320). In this situation, when there exists a plurality of treatment rooms, among the treatment rooms that have selected the same group, in which irradiation can be performed, the treatment room with the highest score is selected as an irradiation subject. Alternatively, considering the case where depending on the contents of therapy, there exist treatment rooms that have the same score, the order of priority may preliminarily be given to the treatment rooms. Further alternatively, the score may take two values (0 and 1) for "irradiation permitted" and "irradiation prohibited".

Accordingly, one treatment room in the group α and one treatment room in the group β are each determined as a time-sharing irradiation subject; in the determined treatment rooms, it is displayed that those treatment rooms have been determined as irradiation subjects, and then therapy is performed (the step S240). As a result, even in the case where the number of the treatment rooms where time-sharing irradiation can be performed is "2", two out of three or more treatment rooms are selected, so that time-sharing therapy can be performed in the two treatment rooms. In contrast, the treatment rooms that have not been determined as the irradiation subject are in the standby mode until the therapy is completed in the other treatment room in the same group.

There will be specifically explained the method in which the irradiation preparation degree is scored in the step S250.

The most intuitive method is to calculate the total sum of square errors between the desired respiration waveform and the actual respiration waveform. Specifically, the method is implemented in the following manner. Letting T denote the respiration period, the total sum Se of square errors at the k-th respiration period is given by the equation (3) that expresses the integral Ie of square errors.

$$Ie = \int_{kT}^{(k+1)T} (b(t) - b_{obj}(t))^2 dt \quad (3)$$

where b(t) is the actual respiration waveform, and $b_{obj}(t)$ is the desired respiration waveform.

Alternatively, when being expressed in a discrete-time basis, the total sum Se is given by the equation (4) below.

$$Se = \sum_{i=kn}^{(k+1)n} (b_i - b_{obj_i})^2 \quad (4)$$

where "n" is the number of samples in a single respiration period.

The score may be obtained through scoring by deducting points in which, for example, the total sum Se of square errors is subtracted from the reference point.

Moreover, as a simpler method, there exists a method in which scoring is implemented by comparing the respiration gate for the desired respiration waveform with the respiration gate for the actual respiration waveform. In this case, it is desirable that the time period in which the respiration gate is ON at both the desired waveform reference and the actual respiration reference in a single respiration period is long. Thus, the time period in which the respiration gate is ON at both the desired waveform reference and the actual respiration reference may be assumed as the score.

It is desirable that in the foregoing scoring, one to two past respiration periods are taken into consideration, in addition to the present respiration period. This is because the state where the respiration condition does not change is a state suitable for beam irradiation.

In the foregoing example, in order to easily understand the treatment rooms, the ON time periods of which overlap with each other, there has been explained a case where a group in which the ON time periods do not overlap with each other is preliminarily prepared; however, the present invention is not limited thereto. For example, in the case where even when the phase of each treatment room is adjusted, the ON time periods overlap with one another (the step S300 in FIG. 5), it is only necessary to select the treatment rooms, among the treatment rooms whose ON time periods overlap with one another, in which irradiation is to be performed.

As described above, the particle beam therapy system according to Embodiment 2 is configured in such a way that the controller 4, in cases where among a plurality of treatment rooms, there exist treatment rooms whose irradiation times TI synchronized with the desired respiration waveform WIb overlap with one another, as when the treatment rooms in the same group are selected, compares the actual respiration waveform measured by the respiration measurement apparatus 22a with the desired respiration waveform WIb of each of the treatment rooms whose irradiation times overlap with one another, and selects, based on the comparison result, a single treatment room, among the treatment rooms whose irradiation times TI overlap with one another, which is to be controlled in a synchronized manner, i.e., which is to be irradiated in a time-sharing manner; therefore, even in the case where the number of treatment rooms is larger than the number of the treatment rooms where concurrent irradiation can be performed, time-sharing irradiation can smoothly be implemented.

Embodiment 3

In the assumption of Embodiment 1 or Embodiment 2, there has been explained a case where time-sharing irradiation can concurrently be performed in two treatment rooms, i.e., in the case where the duty ratio of the respiration gate signal BG is slightly smaller than 0.5. However, as described above, lowering the duty ratio makes the threshold value Th lower and hence the reproducibility of the position-posture of a patient is raised. In a conventional particle beam therapy system, lowering the duty ratio makes one-time therapy time longer and hence the number of patients who can undergo the therapy is reduced; thus, it is required to keep the duty ration high. In contrast, in the case of a particle beam therapy system, according to the present invention, that adopts time-sharing concurrent irradiation, even when the duty ratio is lowered, the number of treatment rooms where concurrent irradiation can be performed increases; therefore, the stability of the position-posture of a patient can be raised while the number of patients who can undergo the therapy is maintained. Thus, the duty ratio of the respiration gate signal can be set to slightly smaller than 0.33 (⅓) with which time-sharing concurrent irradiation can be performed in three treatment rooms. In this case, three desired respiration waveform groups α, β, and γ are created by shifting the phase every 120°, so that time-sharing concurrent irradiation can be performed in up to three treatment rooms.

The respiration gate signal BG can be created without utilizing the threshold value Th. Originally, because the desired respiration waveform WIb is arbitrarily given, the corresponding respiration gate signal BG is also arbitrary. For example, within the region where the desired respiration waveform WIb is lower than the threshold value Th, only the latter half is utilized. This is because it is desired to utilize a region where the desired respiration waveform WIb is as flat as possible and stable. In contrast, as far as the creation of the respiration gate signal for the actual respiration waveform, the method utilizing the threshold value Th can readily be understood.

In the case where four desired respiration waveform groups α, β, γ, and δ are created by setting the duty ratio of the respiration gate signal for the desired respiration waveform to slightly smaller than 0.25 (¼), which is a further lower value, and by shifting the phase every 90°, so that time-sharing concurrent irradiation can be performed in up to four treatment rooms.

Also in the foregoing example, in order to easily understand the treatment rooms, the ON time periods of which overlap with each other, there has been explained a case where a group in which the ON time periods do not overlap with each other is preliminarily prepared; however, the present invention is not limited thereto. For example, in the case where even when the phase for each treatment room is adjusted with the duty ratio set at the present time point, the ON time periods overlap with one another, the duty ratio may appropriately be reduced.

As described above, in the particle beam therapy system according to Embodiment 3, the controller 4, in cases where among a plurality of treatment rooms, there exist treatment rooms whose irradiation times TI synchronized with the desired respiration waveform WIb overlap with one another, is configured so as to perform adjustment in such a way that the proportion of the irradiation time TI, in each of the irradiation apparatuses 22, synchronized with the desired respiration waveform WIb becomes small so that the irradiation times TI do not overlap with one another; therefore, even in the case where the number of subject treatment rooms is larger than the number of the treatment rooms where concurrent irradiation can be performed, time-sharing irradiation can smoothly be implemented.

Embodiment 4

In each of Embodiments 1 through 3, there has been explained a case where the duty ratio in each timing group is evenly divided. However, depending on the patient site, which is an irradiation subject, there are a site, in the vicinity of the lung, that is susceptible to the respiration and a site, in the head or the like, that is insusceptible to the respiration. In other words, the duty ratio in each timing group is not necessarily even. Accordingly, in a particle beam therapy system according to Embodiment 4, timing tables including different duty ratios are preliminarily prepared in the irradiation system common computer (main controller 40). A doctor or the like can select an appropriate timing group in accordance with the patient site, which is an irradiation subject. Alternatively, it may also be allowed that the main controller 40 extracts duty ratio information pieces from information recorded in the treatment planning apparatus and selects an appropriate group from the extracted duty ratio information pieces.

In this case, in accordance with the selected timing-group duty ratio for each treatment room, the main controller 40 adjusts the phase difference of each timing group so that the ON time periods do not overlap with one another. For example, in the case where the duty ratios of the group α, the group β, and the group γ, which are selected in respective three treatment rooms are 0.15, 0.4, and 0.3, respectively, the phases of β and γ are shifted by 72° and 234° with respect to the phase of α, so that time-sharing concurrent irradiation can be performed while the ON time periods of the respective groups are shifted from one another in such a way that the switching timing for 18° is kept.

Moreover, in the case where the sum of the duty ratios of the selected groups exceeds "1", the number of treatment rooms, which are the time-sharing subjects, may appropriately be limited as explained in Embodiment 2 or adjustment may be implemented so as to reduce the duty ratios as explained in Embodiment 3, so that the sum does not exceed "1".

Description of Reference Numerals

1: accelerator (synchrotron)
2: irradiation system (21: irradiation apparatus, 22: navigation function unit (respiration induction apparatus), 22a: respiration measurement apparatus))
3: transport system (31: transport path, 32: switching electromagnet (switching device))
4: control system (controller) (40: main controller)
6: treatment room
C: period
TC: timing of beam-orbit switching by switching electromagnet
Tf: timing at which irradiation apparatus stops irradiation in synchronization with desired respiration wave
TI: irradiation timing synchronized with desired respiration wave
To: timing at which irradiation apparatus starts irradiation in synchronization with desired respiration wave
WIb: desired respiration wave

The invention claimed is:

1. A particle beam therapy system in which a plurality of treatment rooms, each of which has a respiratory induction apparatus for instructing a patient in respiration timing, are provided, in which based on respective phases of the respiration timings, determined in such a way as to be shifted from one another, the plurality of treatment rooms are divided into a plurality of groups, and in which in a time-sharing manner, particle beams are concurrently irradiated onto patients in the respective treatment rooms selected from the plurality of groups, wherein a controller is provided that performs a step in which a single treatment room, as an irradiation subject of time-sharing irradiation, is selected from a group having a plurality of treatment rooms among the plurality of groups, wherein the controller grades respective irradiation readiness degrees of the treatment rooms in said group having a plurality of treatment rooms and selects the single treatment room, based on the graded values, and wherein the irradiation readiness degrees are graded based on a total sum of square errors between a desired respiratory waveform and a real respiratory waveform.

2. A particle beam therapy system in which a plurality of treatment rooms, each of which has a respiratory induction apparatus for instructing a patient in respiration timing, are provided, in which based on respective phases of the respiration timings, determined in such a way as to be shifted from one another, the plurality of treatment rooms are divided into a plurality of groups, and in which in a time-sharing manner, particle beams are concurrently irradiated onto patients in the respective treatment rooms selected from the plurality of groups, wherein a controller is provided to (i) grade respective irradiation readiness degrees of treatment rooms in a group having a plurality of treatment rooms among the plurality of groups and (ii) select, based on the graded irradiation readiness degrees, a single treatment room, as an irradiation subject of time-sharing irradiation, from the group having a plurality of treatment rooms among the plurality of groups, wherein the controller grades the respective irradiation readiness degrees in accordance with the length of a time in which a respiration gate is ON with both a desired waveform reference and a real respiratory reference.

3. The particle beam therapy system according to claim 1, wherein the irradiation readiness degrees is graded taking into consideration not only the present respiration cycle but also one or two times past periods.

4. The particle beam therapy system according to claim 2, wherein the irradiation readiness degrees is graded taking into consideration not only the present respiration cycle but also one or two times past periods.

5. A method of selecting a single treatment room, as a time-sharing irradiation subject, in a group having a plurality of treatment rooms among a plurality of groups in a particle beam therapy system in which a plurality of treatment rooms, each of which has a respiratory induction apparatus for instructing a patient in respiration timing, are provided, in which based on respective phases of the respiration timings, determined in such a way as to be shifted from one another, the plurality of treatment rooms are divided into a plurality of groups, and in which in a time-sharing manner, particle beams are concurrently irradiated onto patients in the respective treatment rooms selected from the plurality of groups, the method comprising the steps of:

grading respective irradiation readiness degrees of the treatment rooms in said group having a plurality of treatment rooms; and selecting the single treatment room, based on the graded values, wherein the irradiation readiness degrees are graded based on a total sum of square errors between a desired respiratory waveform and a real respiratory waveform.

6. A method of selecting a single treatment room, as a time-sharing irradiation subject, in a group having a plurality of treatment rooms among a plurality of groups in a particle beam therapy system in which a plurality of treatment rooms, each of which has a respiratory induction apparatus for instructing a patient in respiration timing, are provided, in which based on respective phases of the respiration timings, determined in such a way as to be shifted from one another, the plurality of treatment rooms are divided into a plurality of groups, and in which in a time-sharing manner, particle beams are concurrently irradiated onto patients in the respective treatment rooms selected from the plurality of groups, the method comprising the steps of:

grading respective irradiation readiness degrees of the treatment rooms in said group having a plurality of treatment rooms; and selecting the single treatment room, based on the graded values, wherein the irradiation readiness degrees are graded in accordance with the length of a time in which a respiration gate is ON with both a desired waveform reference and a real respiratory reference.

7. The method of selecting a single treatment room according to claim 5, wherein the irradiation readiness degrees is graded taking into consideration not only the present respiration cycle but also one or two times past periods.

8. The method of selecting a single treatment room according to claim 6, wherein the irradiation readiness degrees is graded taking into consideration not only the present respiration cycle but also one or two times past periods.

* * * * *